(12) United States Patent
Roberts et al.

(10) Patent No.: US 8,486,245 B2
(45) Date of Patent: Jul. 16, 2013

(54) METHODS FOR MEASURING PHYSIOLOGICAL FLUIDS (75) Inventors: Neil Roberts, Pleasanton, CA (US); Gary Smeaton, Edinburgh (GB)

(73) Assignee: LifeScan, Inc.

( * ) Notice: Subject to any disclaimer, the term of this patent is extended or adjusted under 35 U.S.C. 154(b) by 0 days.

(21) Appl. No.: 13/076,413

(22) Filed: Mar. 30, 2011

(65) Prior Publication Data

US 2011/0174616 A1 Jul. 21, 2011

Related U.S. Application Data (62) Division of application No. 11/252,296, filed on Oct. 17, 2005, now Pat. No. 8,066,866.

(51) Int. Cl.
*G01N 27/327* (2006.01)

(52) U.S. Cl.
USPC ............... 204/403.01; 204/403.04; 204/406

(58) Field of Classification Search
USPC ........... 204/400, 401, 403.1, 403.04, 403.11, 204/406; 205/775, 779; 436/95, 149, 150, 436/14; 422/82.01, 82.02
See application file for complete search history.

(56) References Cited

U.S. PATENT DOCUMENTS

| | | | |
|---|---|---|---|
| 5,112,455 A | 5/1992 | Cozzette et al. | |
| 5,266,179 A | 11/1993 | Nankai et al. | |
| 5,352,351 A * | 10/1994 | White et al. | ............ 204/403.04 |
| 5,366,609 A | 11/1994 | White et al. | |
| 5,565,085 A | 10/1996 | Ikeda et al. | |
| 5,589,045 A | 12/1996 | Hyodo | |
| 5,650,062 A | 7/1997 | Ikeda et al. | |
| 5,708,247 A | 1/1998 | McAleer et al. | |
| 6,046,051 A | 4/2000 | Jina | |
| 6,233,471 B1 | 5/2001 | Berner et al. | |
| 6,241,862 B1 | 6/2001 | McAleer et al. | |
| 6,525,549 B1 | 2/2003 | Poellmann | |
| 6,558,351 B1 | 5/2003 | Steil et al. | |
| 6,733,655 B1 | 5/2004 | Davies et al. | |
| 6,743,635 B2 | 6/2004 | Neel et al. | |
| 6,893,545 B2 | 5/2005 | Gotoh et al. | |
| 6,946,299 B2 | 9/2005 | Neel et al. | |
| 6,964,871 B2 | 11/2005 | Bell et al. | |
| 7,468,125 B2 | 12/2008 | Kraft et al. | |
| 2003/0109798 A1 | 6/2003 | Kermani | |

(Continued)

FOREIGN PATENT DOCUMENTS

| | | |
|---|---|---|
| EP | 1318399 A2 | 6/2003 |
| EP | 1067384 B1 | 12/2003 |

(Continued)

OTHER PUBLICATIONS

IDEM Translation of Japanese Patent Publication No. H7-107531 entitled: "Signal Processor for Biosensor", Applicant: Daikin Industries, Ltd., 13 pages, published Nov. 15, 1995.

(Continued)

*Primary Examiner* — Alex Noguerola
*Assistant Examiner* — Gurpreet Kaur (57) ABSTRACT

Electrochemical measurement techniques for measuring the concentration of an analyte in a physiological fluid sample are described. More particularly, the present invention relates to techniques for distinguishing a signal caused by an extraneous event from a desired information providing signal such as one indicative of a measurement error.

3 Claims, 8 Drawing Sheets

U.S. PATENT DOCUMENTS

| | | | |
|---|---|---|---|
| 2003/0217918 A1 | 11/2003 | Davies et al. | |
| 2004/0064133 A1 | 4/2004 | Miller et al. | |
| 2004/0132203 A1 | 7/2004 | Huang et al. | |
| 2004/0259264 A1* | 12/2004 | Morita et al. | 436/149 |
| 2005/0027463 A1 | 2/2005 | Goode, Jr. et al. | |
| 2005/0043598 A1 | 2/2005 | Goode et al. | |

FOREIGN PATENT DOCUMENTS

| | | |
|---|---|---|
| EP | 1541998 A1 | 6/2005 |
| JP | 62-009265 A | 1/1987 |
| JP | 06-85668 | 3/1994 |
| JP | 1995107531 B2 | 11/1999 |
| JP | 2000258338 A | 9/2000 |
| JP | 2001-330581 | 11/2001 |
| JP | 2005099047 A | 4/2005 |
| WO | WO 0167099 A1 | 9/2001 |
| WO | WO 0173124 A2 | 10/2001 |
| WO | WO 2002057768 A1 | 7/2002 |
| WO | WO 03/034055 A1 | 4/2003 |
| WO | WO 2005054846 A1 | 6/2005 |

OTHER PUBLICATIONS

European Search Report, EP Appln. No. 10180120.7, dated Nov. 10, 2010, Munich, Germany, 4 pages.

European Search Report, EP Appln. No. 06255299.7, dated Jan. 30, 2007, Munich, Germany, 4 pages.

European Search Report, EP Appln. No. 06255300.3, dated Oct. 20, 2009, Munich, Germany, 3 pages.

Chinese Examination Report, application No. 200610064082.1, dated Dec. 31, 2010, Beijing, China, 7 pages.

Japanese Patent Application No. 2006-281183, Notice of Reasons for Rejection dated Jun. 13, 2011, Japanese Patent Office, 4 pages.

* cited by examiner

METHODS FOR MEASURING PHYSIOLOGICAL FLUIDS

CROSS-REFERENCE

This application claims the benefits under 35 U.S.C. §§120 and 121 as a Divisional application of U.S. patent application Ser. No. 11/252,296, filed Oct. 17, 2005, pending, which is incorporated by reference in its entirety herein this application.

TECHNICAL FIELD

The present invention relates to techniques for electrochemically measuring the concentration of an analyte in a physiological fluid sample. More particularly, the present invention relates to techniques for distinguishing a signal caused by an extraneous event from a signal that provides desired information such as one indicative of a measurement error.

BACKGROUND

Measuring instruments that use an electrochemical cell as are typically provided by a disposable test strip or the like are well known and popular with consumers. These instruments are used for the detection of various analyte levels in physiological fluid samples. For example, the concentration of an analyte in a variety of different physiological samples, such as urine, tears, saliva, and the like can be determined with these instruments. One popular application is for determining the concentration of an analyte in interstitial fluid, blood or blood fractions, and more particularly in whole blood.

A typical test strip includes a fluid sample application area that includes an electrochemical cell having a reagent integrated with a pair of electrodes that can be electrically connected to a measuring instrument. In making a measurement, a small volume of a physiological fluid such as blood is applied to the sample application area so it wets the reagent. The measuring instrument applies a potential across the electrodes and the fluid chemically reacts with the reagent in a way that changes a measurable electrical property of the reaction fluid (its conductivity, for example) that can be correlated to a concentration of the analyte of interest. As a result, an electrical characteristic of the reaction fluid (typically its ability to conduct a current) can be measured with a suitable electronic system of the measuring instrument. The measured electrical characteristic is related to the concentration of the particular analyte being measured in the physiological fluid and can be used to determine the concentration of the analyte. For example, in a blood glucose measurement, an oxidation current that is produced can be measured and used to determine glucose concentration in the blood sample.

Typically, the magnitude of the measured current is integrated over a predetermined time period and used to determine a concentration value for the analyte being measured. Because of this, it is important to measure the current after it is known that a sufficient amount of the sample to be measured is present. Thus, many measuring instruments include a way to check for the presence of a fluid sample before initiating measurements that are used to determine analyte concentration.

One way to check for the presence of a fluid sample on a test strip is to apply a potential to the electrodes of the test strip while the measuring instrument is waiting for application of a sample. The presence of a continuous current for a predetermined period of time and above a predetermined magnitude indicates the presence of sufficient sample, which indication can then be used to trigger the start of a measurement cycle. If a short duration current is measured (less than the predetermined period of time), the measuring instrument determines insufficient sample exists and an error condition is generated. While this technique is effective, an extraneous signal or event can lead to such an error condition even when no sample at all is present (with a dry test strip, for example) or when sufficient sample is present. As one example of such an event, electrostatic discharge can, under certain circumstances, provide a false signal. Electrostatic discharge typically provides a short duration current with high voltage within an electrode that may be detected. Thus, it is desirable for the measuring device to be able to distinguish between a short duration current caused by the presence of insufficient sample and to properly indicate a true error condition and a short duration current caused by an extraneous event such as electrostatic discharge.

Electronic hardware devices can be used to filter or suppress extraneous signals such as those caused by electrostatic discharge. However, such hardware based devices are typically non-adjustably configured to provide a specific filtering or suppression function. For example, many hardware filters are designed to simply block a current spike having a predetermined magnitude anytime it occurs and do not have the ability to consider other factors such as when or how long the current spike occurs.

SUMMARY

The present invention therefore provides techniques for distinguishing current signals or spikes caused by extraneous events such as electrostatic discharge or the like from a current signal that provides desired information such as one indicative of a measurement error. Generally, the present invention provides a way to consider the timing, duration, or both of a current signal to determine whether the current signal is due to an extraneous event, that can be ignored, or is related to a measurement event that should provide an indication of an error or problem or the like. For example, a current signal due to electrostatic discharge typically has a shorter duration as compared to a current signal indicative of a lack of sufficient measurement sample or other measurement error. This timing information is used to distinguish between current signals that are provided by extraneous events and those that provide desired information in accordance with the present invention.

In one aspect of the present invention, a method of electrochemically analyzing a physiological fluid sample to determine the concentration of an analyte present in the physiological fluid sample is provided. The method comprising providing a test device comprising a test fluid application portion having at least a pair of electrodes and a reagent. A predetermined potential is provided across the at least a pair of electrodes. A current is detected at the at least a pair of electrodes that is equal to or above a threshold value and the magnitude of the current is monitored over a first time period. Also, a decision is made to perform one of the following: 1) if the magnitude of the current remains above a predetermined value over the first time period, then the magnitude of the current at the end of a second time period is used as a test reading indicative of the concentration of an analyte in a physiological fluid present in the test fluid application area of the test device; and 2) if the magnitude of the current is equal to or below the predetermined value anytime during the first time period, then the step of detecting a current and the step of performing one of the following are repeated.

In another aspect of the present invention, a method of preventing electrostatic discharge from interfering with an electrochemical measurement of the concentration of an analyte in a physiological fluid sample is provided. The method comprises providing a test device comprising a test fluid application portion having at least a pair of electrodes and a reagent. A predetermined potential is provided across the at least a pair of electrodes. A current is measured at the at least a pair of electrodes and the magnitude of the current at the end of a first predetermined time period is used as a test reading indicative of the concentration of an analyte in a physiological fluid present in the test fluid application area of the test device if the magnitude of the current remains above a threshold current value for a second predetermined time period wherein the second time period comprises an initial portion of the first time period.

In yet another aspect of the present invention, a testing meter for electrochemically measuring the concentration of an analyte in a physiological fluid sample is provided. The testing meter comprises a processor, an electrochemical measurement device, and memory. The electrochemical measurement device can be electrically connected to a test device comprising a fluid application portion having at least a pair of electrodes and a reagent so that the electrochemical measurement device can provide a potential and measure current flow across the at least a pair of electrodes when a test device is electrically connected to the electrochemical measurement device. The memory comprises programming that can cause the electrochemical meter, when a test device is electrically connected thereto, to measure a current at the least a pair of electrodes and use the magnitude of the current at the end of a first predetermined time period as a test reading indicative of the concentration of an analyte in a physiological fluid present in the test fluid application area of the test device if the magnitude of the current remains above a threshold current value for a second predetermined time period wherein the second time period comprises an initial portion of the first time period.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1:
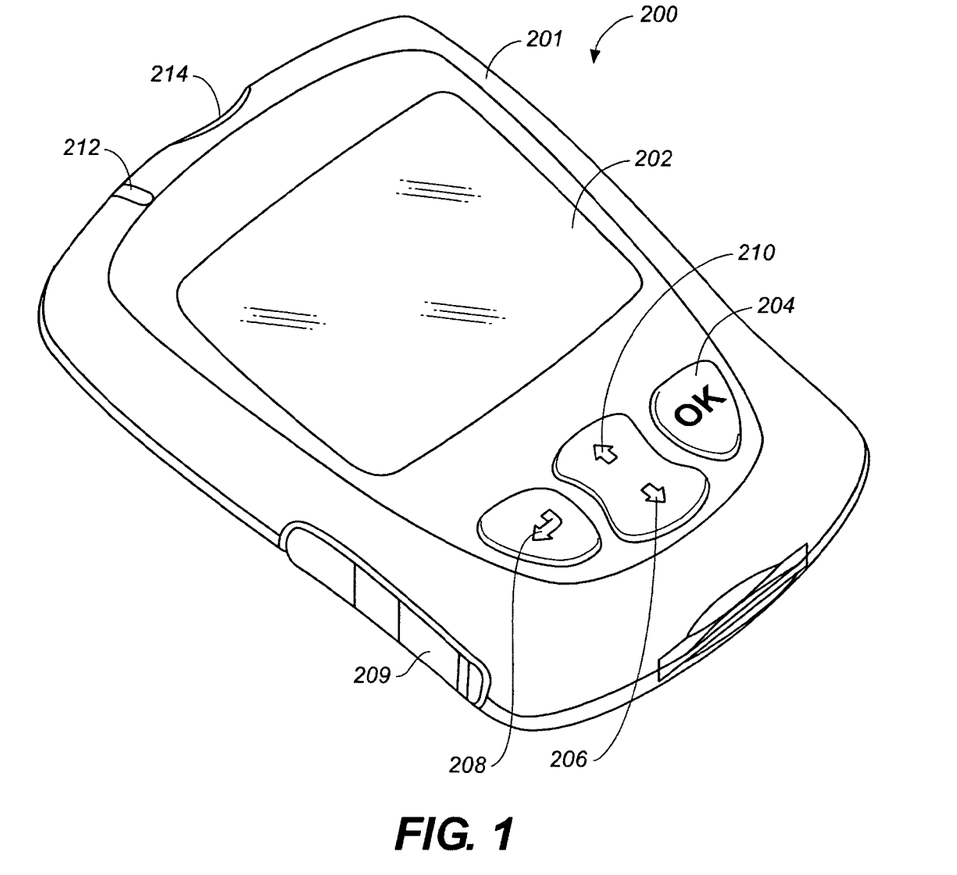
FIG. 1 is a perspective view of an exemplary test meter that can be used in accordance with the present invention.

FIG. 1 is a perspective view of an exemplary test meter 200 in accordance with an exemplary embodiment. Test meter 200 includes a housing 201, a display 202, an OK button 204, a down button 206, a back button 208, an up button 210, a light emitting diode (LED) 212, and a strip port connector (SPC) 214. Display 202 may be a liquid crystal display (LCD) to show both textual and graphical information to a user. A user interface (UI) may be software driven menu that is shown on display 202 that enables the user to operate test meter 200. A user can navigate through the UI using up button 210, down button 206, OK button 204, and back button 208. Test meter 200 is an example of one configuration of a test meter; there may be many others. Housing 201 may be formed from any of a variety of materials, including but not limited to polymeric materials, metals and metal alloys, etc. Display 202 may be any variety of display devices, including, but not limited to LCD displays, LED displays, OLED displays, and other types of displays which may be heretofore developed. Further, display 202 may be a series of lights and/or simple readouts as opposed to a single integrated display screen. LED 212 may be any other variety of indicators, including, but not limited to LED's, other types of light devices, sound devices, vibration devices, etc. Strip port connector 214 is used to accept and to electrically connect a test strip to test meter 200 however other configurations of interfacing devices may also be used. Buttons 204, 206, 208, and 210 may be any of a variety of buttons or other user input devices including, but not limited to touch sensitive devices. Further, buttons 204, 206, 208, and 210 may be replaced a user interface on display 202 or a speech recognition device built into test meter 200. Display 202 may also include a touch sensitive screen which overlays display 202 and allows a user to provide input to test meter 200 via the touch screen. In an exemplary embodiment, the touch sensitive screen may be used with a user's finger, a separate stylus or other touching device.

Figure 2:
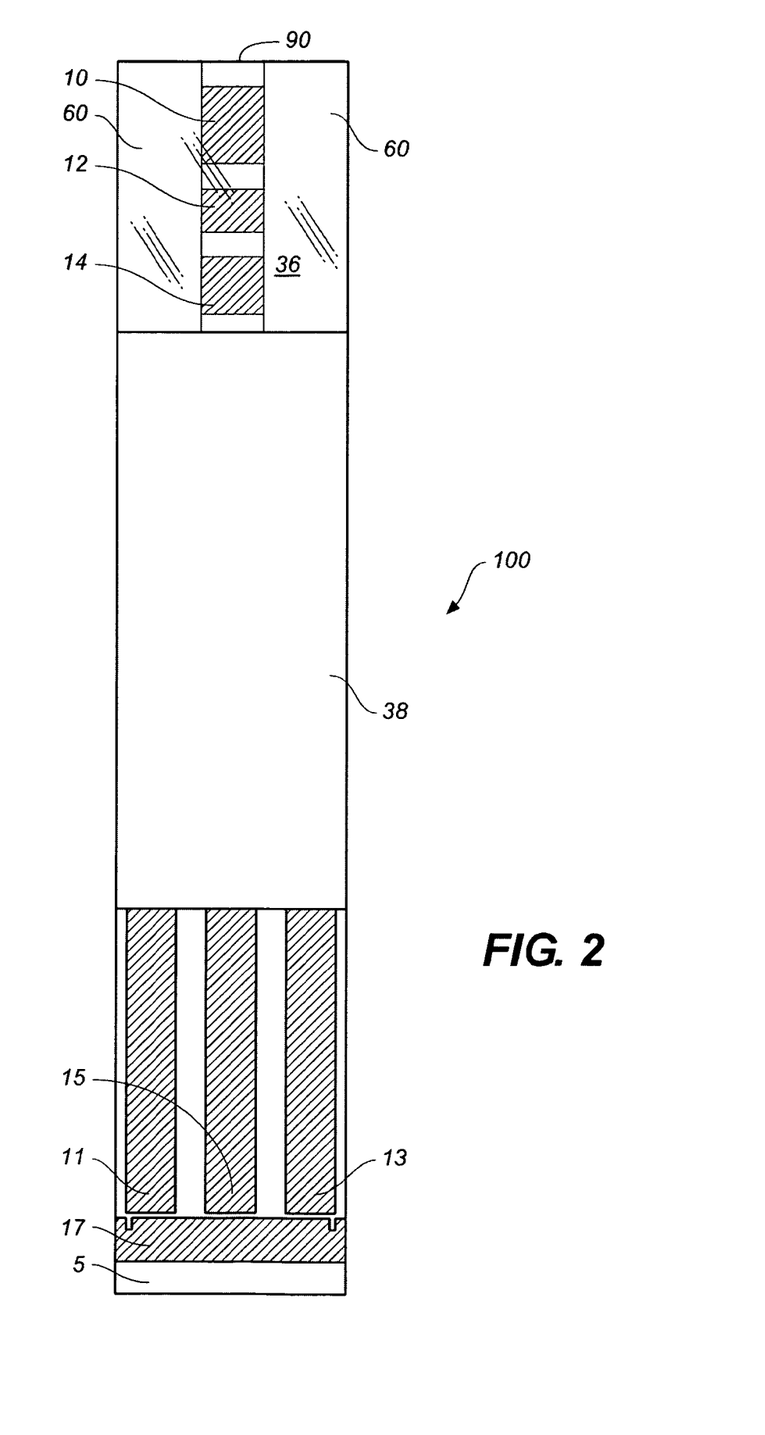
FIG. 2 is a plan view of an exemplary test strip that can be used in the test meter of FIG. 1 having a first working electrode, a second working electrode, and a reference electrode.

A test strip 100 suitable for use in test meter 200 is shown in FIG. 2. Test strip 100 includes a conductive layer comprising electrically isolated portions that are conventionally printed onto a substrate 5. The conductive layer includes a first contact 13, a second contact 15, a reference contact 11, and a strip detection bar 17, which may be used to electrically connect to strip port connector 214. The conductive layer further includes a first working electrode 12, a second working electrode 14, and a reference electrode 10 which are electrically connected, respectively, to first contact 13, second contact 15, and reference contact 11. Contacts to the electrodes connect within the meter to apply a voltage across electrodes selectively under control of the meter. Test strip 100 further includes, but is not limited to, a clear hydrophilic film 36 which is bound by an adhesive 60 that forms a sample receiving chamber that allows blood to be dosed at an inlet 90. In an exemplary embodiment film 36 covers the entire end of the test strip thereby forming the visible sample chamber between the adhesion zones shown as 60 in FIG. 2. An opaque film 38 is also bound by adhesive 60 to show contrast for guiding user to dose blood at inlet 90. Substrate 5 may be formed of a variety of materials including, but not limited to polymeric materials or other insulating materials. In an exemplary embodiment, the material substrate 5 may be formed from a polyester material (such as, but not limited to Meline ST328), which is manufactured by DuPont Teijin Films. Substrate 5 may be supplied in a roll of material, which may be, for example, nominally 350 microns thick by 370 millimeters wide and approximately 660 meters in length. Conductive layers, such as layers 10, 11, 12, 13, 14, 15, and 17 may be formed from any of a variety of conductive materials such as, but not limited to metals and metal alloys which may be deposited on substrate 5 via any of a number of manufacturing processes. Opaque film 38 is used for the convenience of a user to provide contrast but may be substituted by any of a number of methods, such as printed textual indicators, to guide the user to dose blood at inlet 90. An example of test strip 100 is OneTouch Ultra which is available from LifeScan, Inc. (Milpitas, Calif., USA).

In accordance with an alternative exemplary embodiment, it may be desirable to provide a test strip which includes a working electrode and a reference electrode, as opposed to two working electrodes. Further, any of a variety of test strip configurations may be suitably substituted for test strip 100 without departing from the scope of the invention as long as test strip 100 is able to provide an electrical signal to test meter 200 when a physiological fluid sample is present.

A reagent layer (not shown) may be disposed on first working electrode 12, second working electrode 14, and reference electrode 10 within the sample chamber or cavity. Reagent layer may include chemicals such as a redox enzyme and mediator which selectively reacts with glucose. Examples of reagent formulations or inks suitable for use in making reagent layer 22 can be found in U.S. Pat. Nos. 5,708,247 and 6,046,051; Published International Applications WO01/67099 and WO01/73124, all of which are incorporated by reference herein. Further, any of a variety of other reagent layers and reagent chemicals may be used without departing from the scope of the invention. Alternatively, it may be possible to produce a test strip that does not utilize a reagent layer as disclosed in the references provided. Further still, it may not be required to have the reagent layer disposed on all of the electrodes 12, 14, and 10. Rather, the reagents may be disposed on any of the electrodes or other surfaces within the sampling region of the test strip.

Once test strip 100 is electrically connected to test meter 200 through strip port connector 214, a user may apply a physiological fluid to inlet 90. In accordance with alternative embodiments, test meter 200 may have different types of connectors as opposed to strip port connector 214. The scope of the invention may not be limited by the type of connector being used. Physiological fluid may be applied to test strip 100 in a variety of ways. The fluid sample may be taken from a droplet of blood on the skin surface, or from a receptacle. A physiological fluid sample may also be taken directly from the body by using a needle or microneedle. The physiological fluid causes the reagent layer to dissolve and enzymatically generate a proportional amount of reduced mediator which correlates to a glucose concentration. Test meter 200 may apply a test voltage of about +0.4 Volts, for example, between first working electrode 12 and reference electrode 10. The test meter can also apply a test voltage of about +0.4 Volts between second working electrode 14 and reference electrode 10. This will enable the reduced mediator to be proportionally measured as a test current, which in this case is an oxidation current measured at first working electrode 12 and at second working electrode 14. In accordance with alternative embodiments, the test voltage that is applied may be any of a variety of test voltages. The test voltages are not limited to the 0.4 Volts described above. Further, it may not be necessary to apply test voltages between both a first electrode and the reference electrode and a second electrode and the reference electrode. It may be desirable only to have a system which measures voltages between the first electrode and the reference electrode, thereby simplifying the system.

Figure 3:
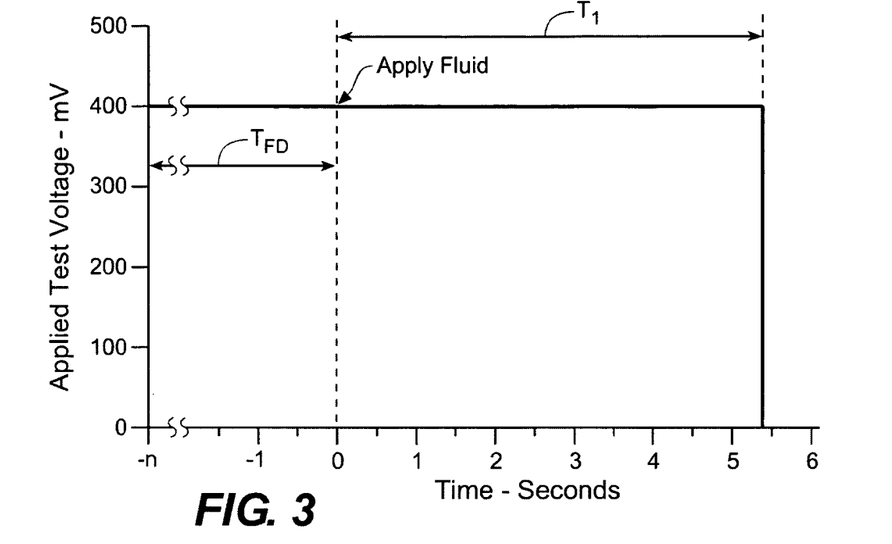
FIG. 3 is a diagram showing the relationship between a test potential applied to the exemplary test strip of FIG. 2 and time for an exemplary measurement test in accordance with the present invention showing in particular a fluid detection time interval before a fluid is applied to the test strip and a test time interval T1 after the fluid is applied to the test strip.

FIG. 3 is an exemplary chart showing a test voltage applied by test meter 200 to test strip 100 for a test time interval T1. Before the physiological fluid is applied, test meter 200 would be in a fluid detection mode in which the test voltage is +0.4V. The fluid detection mode is indicated in FIG. 3 as a fluid detection time interval TFD and as indicated is a time period before or less than a zero (0) reference time. In the fluid detection mode, test meter 200 determines when a fluid is applied to inlet 90 such that both first working electrode 12 and reference electrode 10 are wetted with a fluid. Note that first working electrode 12 and reference electrode 10 are effectively short-circuited when the physiological fluid contiguously covers first working electrode 12 and reference electrode 10. Once test meter 200 recognizes that the physiological fluid has been applied because of a sufficient increase in the measured test current between electrodes 10 and 12, test meter 200 assigns a zero second marker and starts the test time interval T1. In accordance with other exemplary embodiments, other methods of determining the presence of a physiological fluid on the test strip may be used. For example, other methods of detecting the presence of a fluid on the test strip may be used. Further, it may be possible to manually indicate to the test meter when to start the test time interval. Accordingly, although the described methodology for detecting an applied fluid and for determining when to start the test time interval, may be effective, other methods either known or later developed may be used without departing from the scope of the invention.

In an exemplary embodiment of this invention, test time interval T1 may be about 5.4 seconds. During the first time interval, the sample current is measured and the data collected to determine the glucose concentration in the sample. Upon the completion of the test time interval T1, the test voltage is removed. While an effective test time has been shown to be 5.4 seconds, any of a variety of test times may be used.

Figure 4:
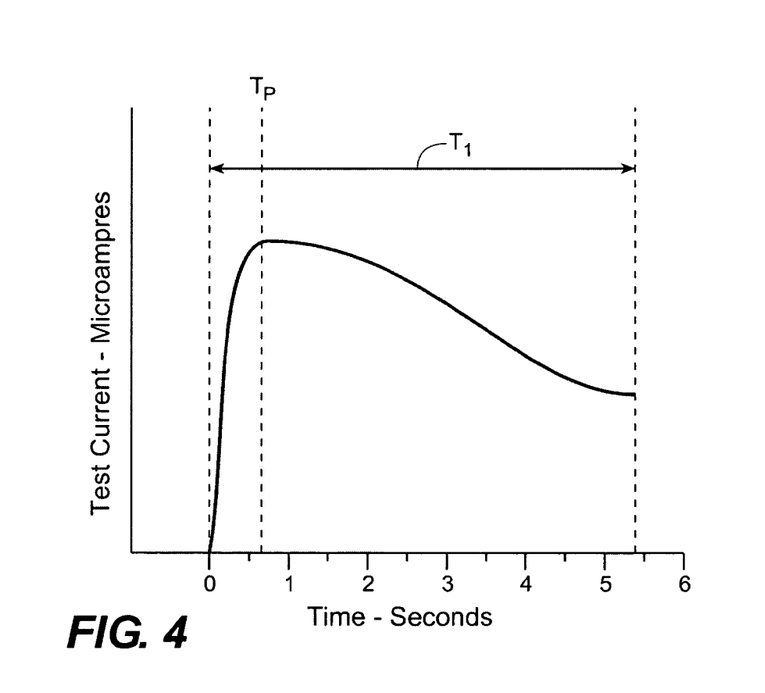
FIG. 4 is a diagram showing the relationship between a test current produced by the test strip and time for the exemplary measurement test illustrated in FIG. 3 during the test time interval T1.

In accordance with an exemplary embodiment, test strip 100 will carry a test current when the test voltage is sufficiently positive with respect to a redox potential of the mediator. Note that a redox potential describes a mediator's intrinsic affinity to accept or donate electrons when sufficiently close to an electrode having a nominal potential. FIG. 4 is an exemplary chart showing the test current detected flowing through the sample on test strip 100 for test time interval T1.

The meter coupled to test strip 100 is configured to measure the current in the circuit formed by the two electrodes and the sample in the sample area. In general, the test current rapidly increases when test strip 100 is initially wetted with the physiological fluid causing a peak to be formed which is followed by a gradual decrease in the test current. While FIG. 4 represents a typical test, other response curves may be observed, especially but not only, in the testing for other analytes besides glucose as well as the presence of other noise disturbances.

The present invention is particularly useful for distinguishing current signals caused by extraneous events from a current signal that provides desired information such as one indicative of a measurement error. Extraneous signals can come from a variety of sources, events, or conditions and typically occur during the normal use of a test meter such as the test meter 200. Exemplary extraneous events include electrostatic discharge and electromagnetic emission such as radio-frequency or microwave frequency emission, for example. Use of an electronic device such as a phone, microwave oven, radio, or other household appliance can potentially cause an extraneous signal. Also, common events such as switching of light switches, switching of thermostats, and other activities were an electronic relay or the like turns on an off can cause extraneous signals.

In accordance with the present invention, a particular extraneous signal can be characterized in some way and used to distinguish the extraneous signal from a desired signal. Characterization in this way preferably relates to the magnitude, duration, and timing (independently or in combination) of an extraneous signal. Generally, a characteristic behavior of an extraneous signal or event can be used to identify the signal as extraneous. This behavior may be a specific value or may relate to a trend or changing condition over time, for example.

One type of extraneous signal is related to electrostatic discharge. Under certain conditions, such as where low relative humidity exists, a user can carry a significant amount of electrostatic charge. Thus, such a user may potentially inject electrostatic energy into the test meter, when touching a test strip connected to a test meter. This unexpected energy can cause the meter to measure a sufficiently large current that can cause the meter to initiate and perform a glucose test on a dry test strip. Because there is no glucose in the test strip, the meter should output an error message because the measured test current will be too low. Typically, a user will be instructed to discard the test strip when the meter generates an error message. This is highly undesirable where ESD falsely triggers a glucose test because the dry test strip is actually not defective and thus would be thrown away unnecessarily.

Figure 5:
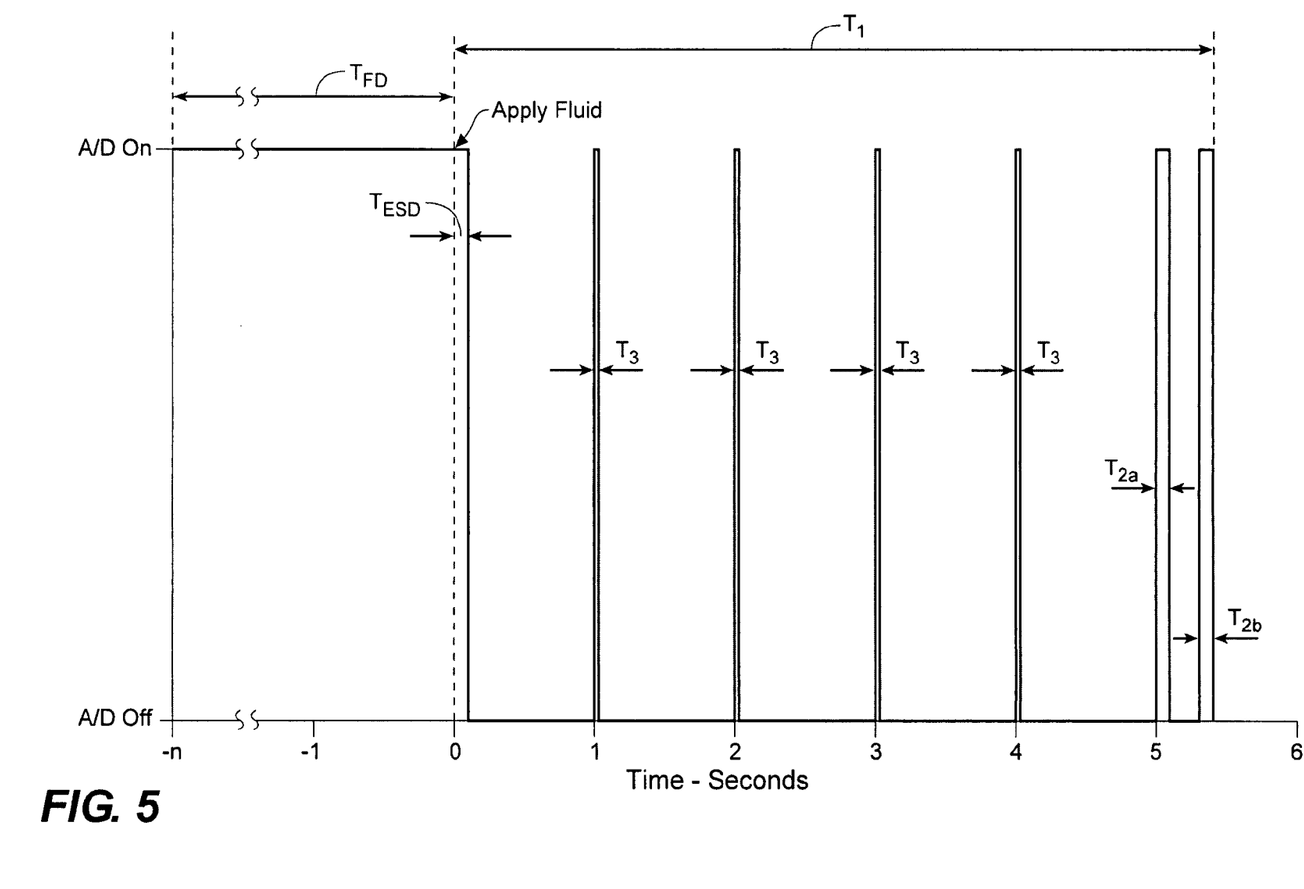
FIG. 5 is a diagram of the exemplary measurement test illustrated in FIG. 3 graphically showing as part of the test time interval T1 an electrostatic discharge check time interval TESD, a plurality of test current reading time intervals T1, a final current value time interval for the first working electrode T2a, and a final current value time interval for the second working electrode T2b, in accordance with the present invention.

In use, test meter 200 preferably starts a fluid detection mode once test strip 100 is inserted into strip port connector 214. During the fluid detection mode, test meter 200 preferably applies a test potential of between at least the first working electrode 12 and the reference electrode 10. The test voltage used generally depends of the particular test meter and test strip used and a suitable test voltage for the illustrated meter 200 is about 400 millivolts. The fluid detection mode time interval TFD includes the time before physiological fluid is applied to inlet 90 and is represented as the time interval that is less than zero as illustrated in FIG. 5. During fluid detection mode time interval TFD, test meter 200 will preferably continuously measure a current reading at a predetermined frequency until a single current reading is found to exceed a threshold value. As an example a measurement frequency ranging from about once every 20 milliseconds to about once every 100 milliseconds can be used. A threshold value that can be used for testing blood is about 150 nanoampres. When test strip 100 is initially dry, test meter 200 will measure a zero test current value or a small test current value which is below the threshold. Once fluid is applied, the test meter will measure an increase in a current reading due to a decrease in resistance between the first working electrode 12 and reference electrode 10. This current increase will cause the meter to start test time interval T1 as shown in FIG. 5.

As a precautionary measure, test meter 200 preferably enters an ESD check mode in accordance with the present invention once test meter 200 measures at least one current reading greater than the threshold as shown in FIG. 5. In the ESD check mode, test meter 200 preferably continues to apply a potential for an ESD check time interval TESD. During the ESD check mode, test meter 200 preferably continuously measures a current reading on a predetermined schedule. For example, a measurement once every 20 milliseconds can be used. If any of the current readings measured during ESD check time interval TESD are less than the threshold, then test meter 200 preferably returns back to the fluid detection mode. If all of the current readings measured during ESD check time interval TESD are greater than the threshold, then test meter 200 will continue the glucose test.

For the case in which a physiological fluid such as blood is applied to test strip 100, a test current will be seen to increase for about 1 second as shown in FIG. 4. Therefore, test meter 200 will measure an increase in a current reading of greater than about 150 nanoampres due to a decrease in resistance between the first working 12 electrode and reference electrode 10. This will preferably cause the meter to go from the fluid detection mode to the ESD check mode. Typically, the test current will stay greater than 150 nanoampres for the ESD check time interval TESD allowing the glucose test to proceed through the test time interval T1.

For the case in which a sufficiently large ESD is injected into test meter 200, a current reading may be measured that is greater than the threshold causing the meter to go from the fluid detection mode to the ESD check mode. Typically, a test current generated by ESD dissipates quickly producing a transient spike that typically decays within about a 100 millisecond range. This contrasts with the increase in the test current caused by a test fluid such as blood where the test current continues to increase beyond a threshold of 150 nanoampres for a known time for the particular fluid (about 1 second for blood). Thus, when ESD is injected into test meter 200, at least one of the current readings measured during ESD check time interval TESD should be less than the threshold. Once test meter 200 measures a current reading less than the threshold, test meter 200 will preferably set a flag. When the ESD check time interval TESD expires, the flag is checked and if set, operation reverts back to looking for sample again. If the flag is not set, fluid measurement preferably continues as described below.

Preferably, where a fluid such as blood is being measured, ESD check time interval TESD ranges from about 100 milliseconds to about 1 second, and preferably be about 200 milliseconds. The low end of ESD check time interval TESD is based on a typical dissipation time of ESD, which is about 100 milliseconds but may be based on a typical characteristic such as a dissipation time for any desired extraneous event. The high end of ESD check time interval TESD is preferably based on the amount of available time before test meter 200 needs to notify a user that the test is in progress. For example, when a test meter performs a glucose test, a countdown of test time interval Ti is typically outputted onto a display of the test meter 200 in integer values. After one second has elapsed on the display, the user will believe that the glucose test is in progress. Therefore, when a sufficiently large amount of ESD is injected into test meter 200, it needs to determine that it must go back to the fluid detect mode before the user has any indication that the test is in progress such as when the display shows that one second of the glucose test has elapsed.

A meter, such as the meter 200, can be programmed so that after a first trigger reading (a measurement above a predetermined threshold) the meter continues to monitor the current for some predetermined period of time. The threshold may be a current level indicative of the presence of a sample for example. If during the monitoring period the current falls below the trigger threshold, the meter will set a flag. When the monitoring time expires, the flag will be checked and if set, operation will revert back to looking for sample again. If the current remains above the threshold for the whole of this period then the test sample current readings can be processed as normal. Monitoring the current for the whole of the ESD check period instead of reverting back once ESD is first detected can ensure that any ringing of the ESD pulse has time to decay before the meter attempts another reading.

It should be noted that the test current in FIG. 4 is an analog signal that may be converted to a digital signal for processing the test current into a glucose concentration. In an exemplary embodiment of this invention, test meter 200 may include a Texas Instrument mixed signal processor (e.g. TI MSP 430) having a twelve bit A/D converter for converting the analog test current into a digital test current. Other A/D converting circuits may similarly be used, including those with more or less bits providing differing accuracy and resolution, and those made or provided by different manufacturers. In an exemplary embodiment of this invention, the test current must be measured with a sufficiently high signal to noise (S/N) ratio such that a variation of the acquired digital signal may be less than about 5% CV (coefficient of variation, % CV={one standard deviation/average}×100), preferably less than about 3% CV, more preferably less than about 1% CV, and even more preferably less than about 0.1% CV. Other S/N ratios may be used, not limited to those explicitly provided. Further, although characterized by % CV, other characterizations of S/N ratio may also be used without departing from the scope of the invention. In an exemplary embodiment, a method will be described that reduces the noise in sampling the test current using an A/D converter.

Figure 6:
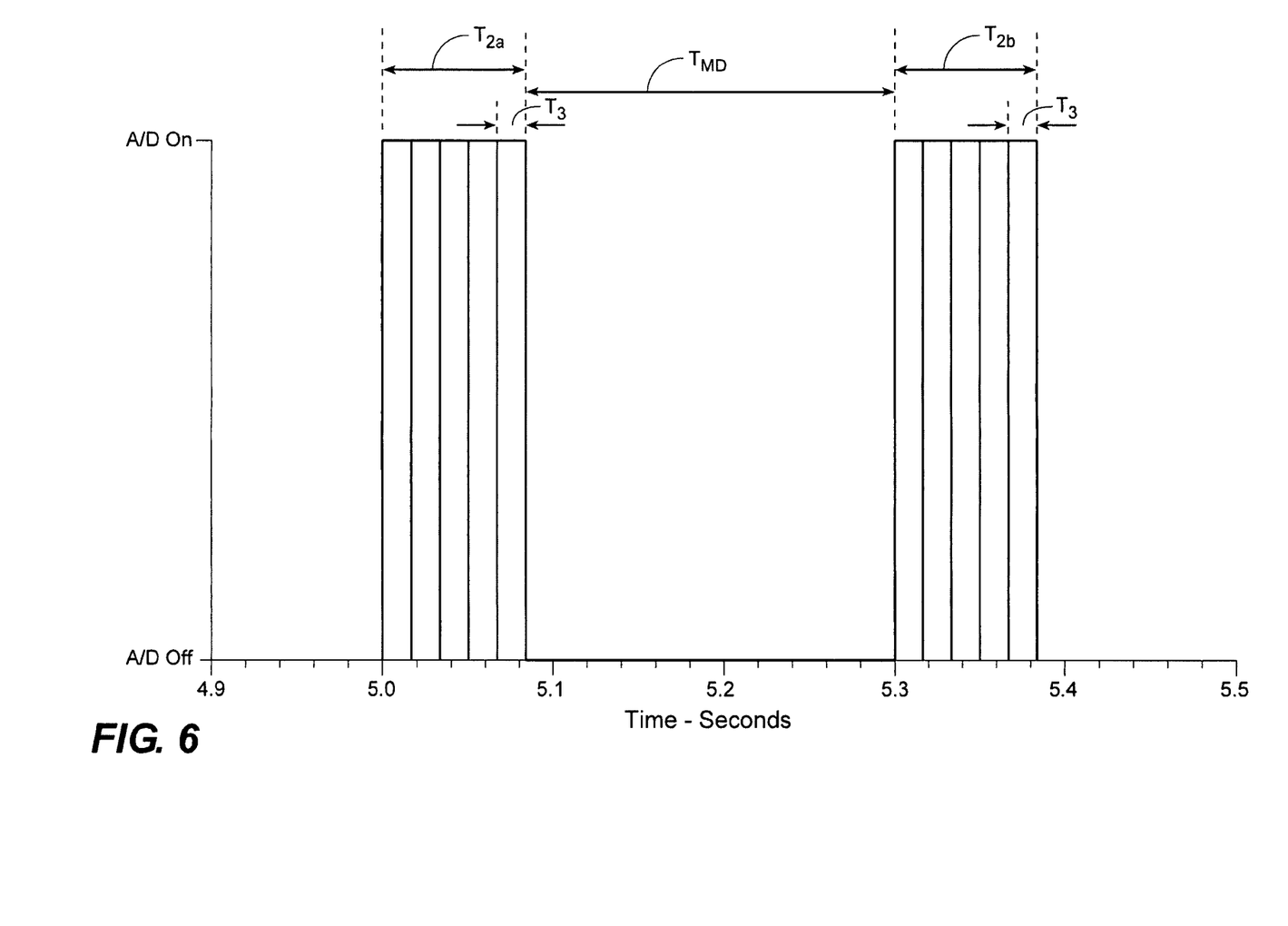
FIG. 6 is a diagram of the final current value time interval for the first working electrode T2a as comprising plural consecutive current reading time intervals T3 and the final current value time interval for the second working electrode T2b as comprising plural consecutive current reading time intervals T3 wherein the final current value time intervals for the first and second working electrodes are separated by a measurement delay time interval in accordance with the present invention.
Figure 7:
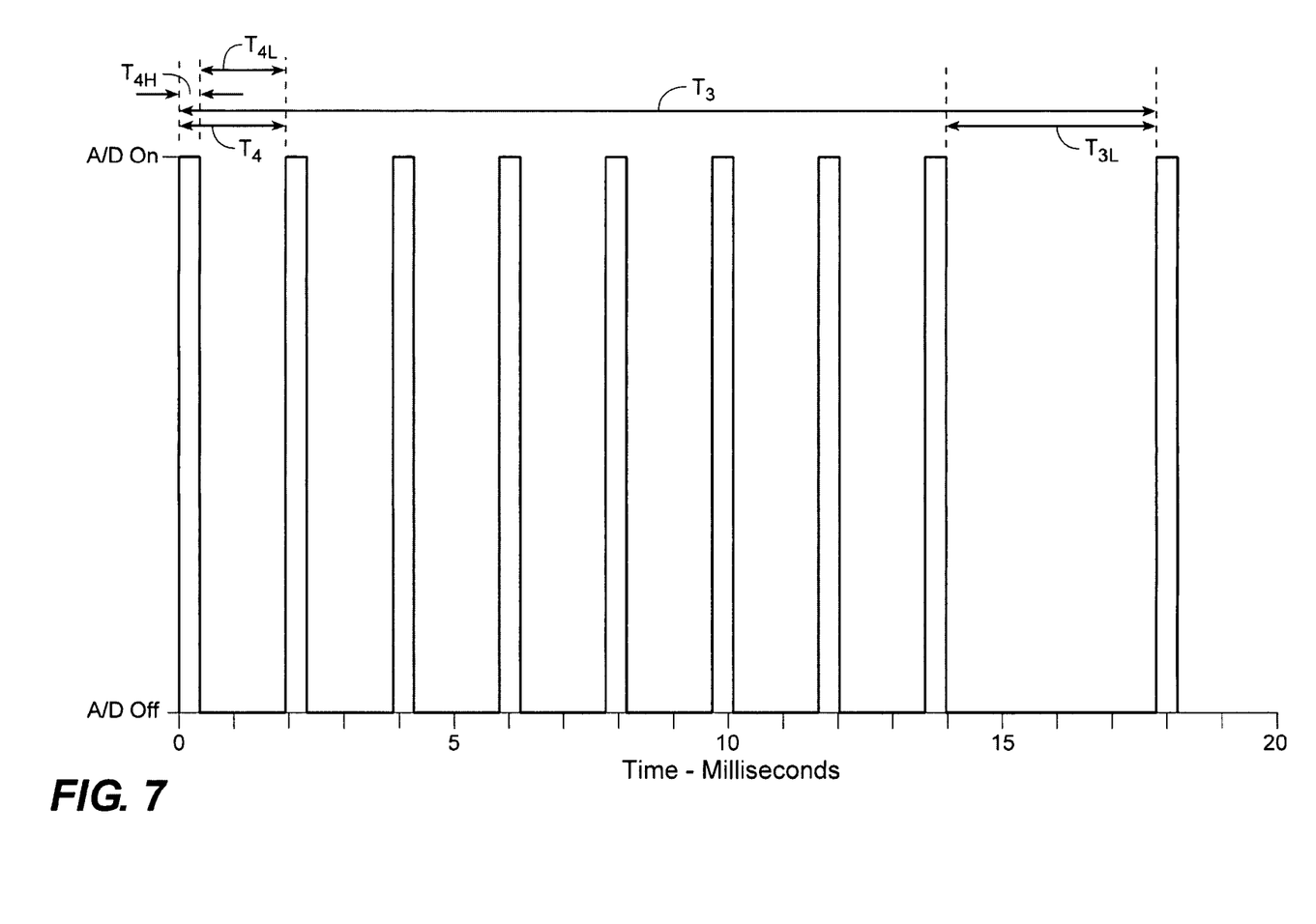
FIG. 7 is a diagram of a current reading time interval T3 of the final current value time intervals for the first and second working electrodes of FIG. 6 and as comprising plural consecutive current sample time intervals T4 in accordance with the present invention.
Figure 8:
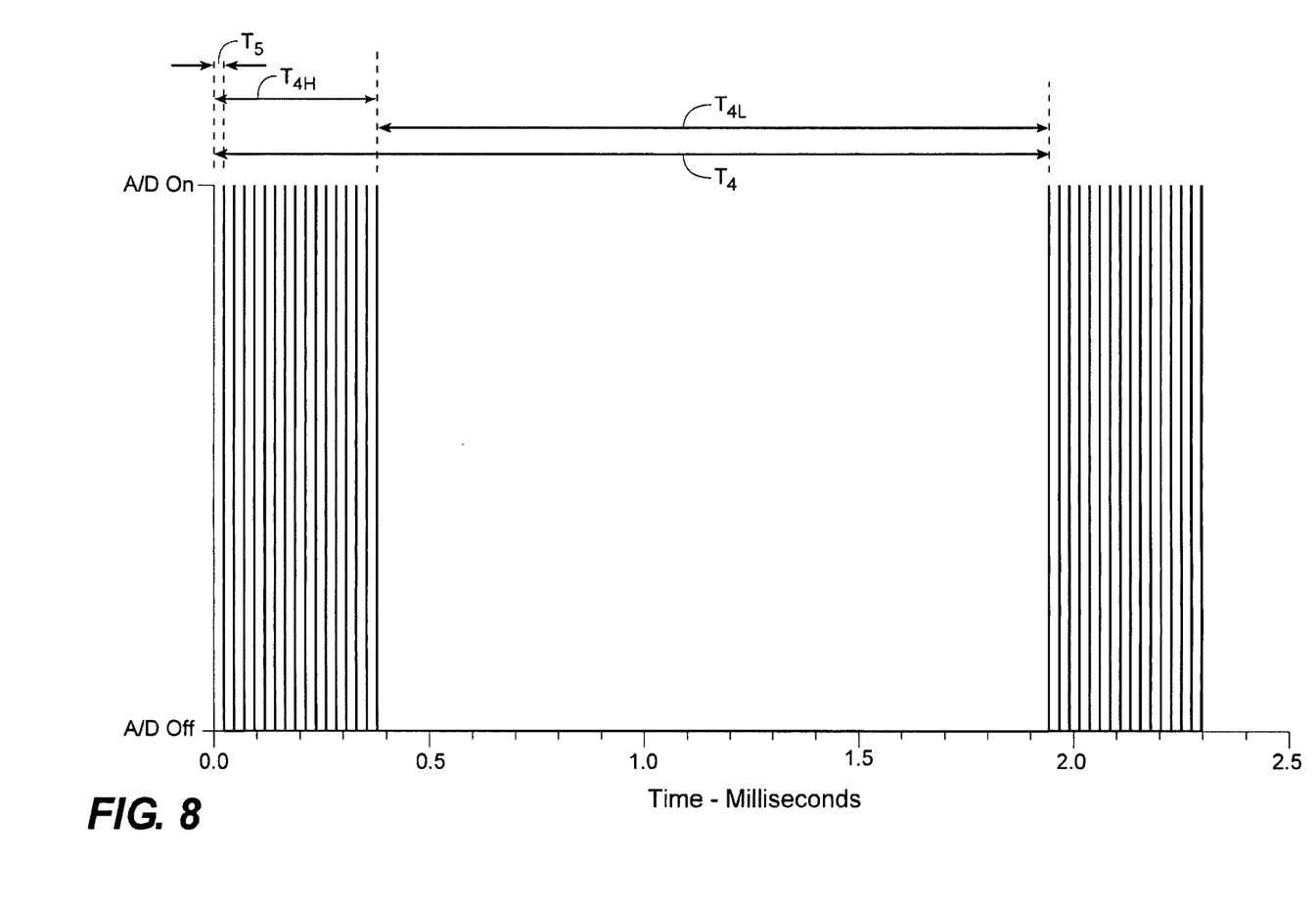
FIG. 8 is a diagram of a current sample time interval T4 of FIG. 7 as comprising plural consecutive analog to digital conversion time intervals T5 in accordance with the present invention.

FIG. 5 is an exemplary simplified chart showing a plurality of time intervals for sampling the test current for a glucose test in accordance with an exemplary embodiment. Test time interval T1 may include an aggregate of shorter time intervals which are a current reading time interval T3, the electrostatic discharge (ESD) check time interval TESD discussed above, a final current value time interval for first working electrode T2a, and a final current value time interval for second working electrode T2b. Alternatively, other combinations of time intervals may be used having differing relative lengths. Further, some time intervals may be omitted in alternative embodiments. In FIG. 5, the A/D may toggle relatively quickly between the On and Off state during a given time interval, typically on the order of milliseconds or, in alternative embodiments on the order of microseconds. However, in FIG. 5 the shorter time intervals are shown as being continuously On because the time scale of the chart cannot clearly show a relatively high toggle rate. Note that FIGS. 6 to 8 show expanded portions of T2a, T2b, and T3 to illustrate more accurately if a particular time interval has a higher switching frequency of the A/D conversions between the On and Off state. It should be noted that the sampling frequencies are not limited to those depicted, rather any frequencies may be used that yield desired performance.

FIG. 6 is an expanded simplified view of final current value time interval for first working electrode T2a and final current value time interval for second working electrode T2b. In an exemplary embodiment of this invention, final current value time interval for first working electrode T2a starts at about 5 seconds and has a duration of about 80 milliseconds. Similarly, final current value time interval for second working electrode T2b starts at about 5.3 seconds and has a duration of about 80 milliseconds. There may be a measurement delay time interval TMD of about 300 milliseconds between final current value time interval for first working electrode T2a and final current value time interval for second working electrode T2b. The invention is not limited to those specific time periods provided above, rather any time periods may be used that yield desired performance.

In an exemplary embodiment, a method for sampling a test current at a predetermined sampling rate will be described. This material is also described in U.S. application Ser. No. 11/252,216, entitled "A System and Method of Processing a Current Sample for Calculating a Glucose Concentration," filed on the same day herewith and herein incorporated by reference in its entirety for all purposes. Final current value time interval for first working electrode T2a may include, for example, five consecutive current reading time intervals T3. Similarly, final current value time interval for the second working electrode T2b may include, for example, five current reading time intervals T3. Current reading time interval T3 may be, for example, about 18 milliseconds as shown in FIGS. 6 and 7. The invention is not limited to the numbers of current reading time intervals disclosed nor to the reading time interval disclosed.

FIG. 7 is an expanded simplified view of a current reading time interval T3 which includes eight consecutive current sample time intervals T4. There is a LOW period reading time interval T3L that represents a period of time in which the A/D is Off after acquiring the A/D conversions, for example, for eight current sample time intervals T4. During LOW period reading time interval T3L, the microprocessor has a free time period to perform data calculations such as, for example, a summation or average of the A/D conversions acquired during current reading time interval T3. At the end of LOW period reading time interval T3L, the microprocessor may initiate another current reading time interval T3. Again, the invention is not limited to the time intervals shown and disclosed nor to the number of A/D conversions shown and disclosed.

Current sample time interval T4 may be, for example, about 2 milliseconds as shown in FIGS. 7 and 8. Current sample time interval T4 includes a HIGH period sample time interval T4H and a LOW period sample time interval T4L. HIGH period sample time interval T4H may be a period of time in which the A/D is On for acquiring A/D conversions. LOW period sample time interval T4L may be a period of time in which the A/D is Off after acquiring the required A/D conversions during HIGH period sample time interval T4H. HIGH period sample time interval T4H may be, for example, about 0.4 milliseconds and LOW period sample time interval T4L may be, for example, about 1.6 milliseconds as shown in FIGS. 7 and 8. During LOW period sample time interval T4L, the microprocessor has a free time period to perform data calculations on the acquired A/D conversions acquired during HIGH period sample time interval T4H such as, for example, ranking, filtering, summations, averaging and/or combinations thereof of the A/D conversions or other needed calculations and data manipulations. At the end of LOW period sample time interval T4L, the microprocessor may initiate another current sample time interval T4. The sample time interval magnitudes shown and described are not limited. Any time intervals maybe used which would provide desired performance.

FIG. 8 is an expanded view of an exemplary current sample time interval T4 which includes 16 consecutive A/D conversion time intervals T5. The test current may be sampled at a pre-determined sampling rate during HIGH period sample time interval T4H. The pre-determined sampling rate may be, for example in an exemplary embodiment, about 40 Kilohertz as shown in FIG. 8. A single A/D conversion may be acquired during A/D conversion time interval T5 which in this case may be about, for example, 25 microseconds as shown in FIG. 8. An A/D conversion would be a digital number having a magnitude which is proportional to the test current at the point in time in which the A/D conversion was taken. A/D conversions may also be referred to as a glucose signal because the magnitude of the A/D conversion in this case is proportional to the glucose concentration. Thus in accordance with an exemplary embodiment, 16 A/D conversions may be acquired during current sample time interval T4 and stored in a memory portion of test meter 200. A current sample may then be calculated using either an average or summation of the 16 A/D conversions acquired during current sample time interval T4. In an embodiment of this invention for reducing noise, a current sample may be calculated using either an average or summation of a subset of the 16 A/D conversions acquired during current sample time interval T4. In an embodiment of the present invention, a method will be described that shows how to select a subset of the 16 A/D conversions for reducing the noise when measuring a "current reading." In accordance with alternative embodiments, it may be desirable to discard one or more of the 16 samples acquired for the noise filtering process. Further, it may also be desirable to use more or less than 16 A/D conversions to meet desired performance goals and statistically significant objectives.

Figure 9:
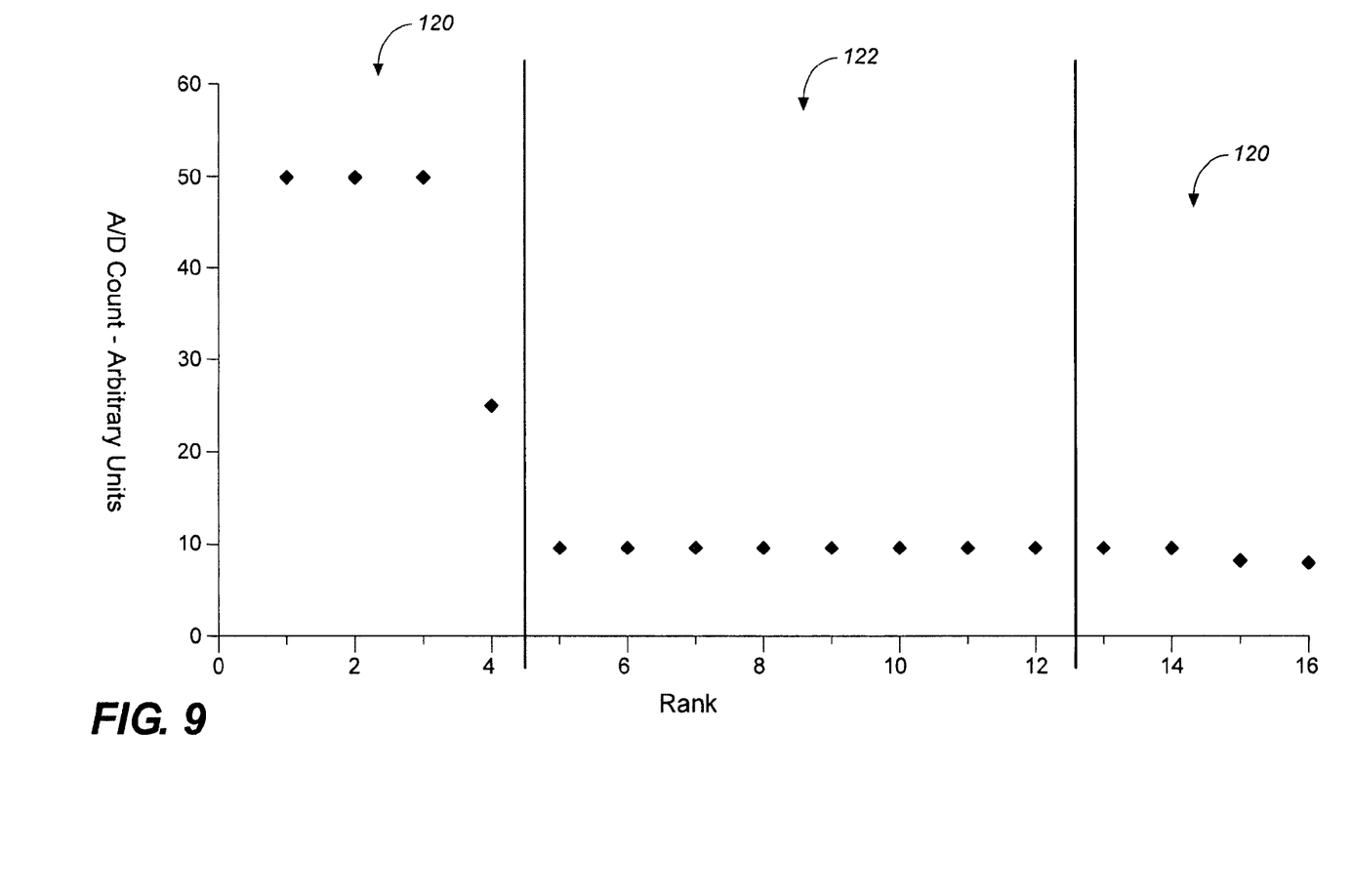
FIG. 9 is a diagram illustrating a non-parametric method of filtering the plural consecutive analog to digital conversion time intervals T5 of FIG. 8 of a current sample time interval T4 in accordance with the present invention.

In general, an exemplary method for reducing noise is to average a plurality of A/D conversions. However, averaging will effectively reduce noise when it follows a Gaussian distribution. For situations in which the noise does not follow a Gaussian distribution, non-parametric methods may be used to help reduce noise. An example of noise which does not follow a Gaussian distribution may be an electrostatic discharge event, signals from light switches, and mobile phones. In an exemplary embodiment, sixteen A/D conversions collected during a current sample time interval T4 may be ranked based on their magnitude as shown in FIG. 9. Instead of simply averaging all sixteen A/D conversions, at least a highest magnitude A/D conversion and a lowest magnitude A/D conversion may be filtered leaving a plurality of accepted A/D conversions. In an exemplary embodiment, only the accepted A/D conversions would be averaged or summed together. Because the highest and lowest A/D conversions are discarded, this makes the average more robust to extreme outliers which may be caused by short term events such as electrostatic discharge. In general, extreme outliers tend to significantly perturb averages making Gaussian statistics ineffectual. Although 16 samples provide good performance in the system described, the invention is not limited to 16 samples. Depending on the desired performance and the application of the filter other numbers of samples may be found to be more or less effective.

In another exemplary embodiment, a four highest A/D conversions and a four lowest A/D conversions may be filtered leaving eight accepted A/D conversions as shown in FIG. 9. FIG. 9 depicts high and low filtered zones 120 and an accepted zone 122. Filtered zone 122 shows the eight remaining samples that will be used for averaging while zones 120 show the eight samples which will be discarded. The microprocessor of test meter 200 may calculate a current sample by averaging or summing together the 8 accepted A/D conversions acquired during current sample time interval T4. Next, a current reading may be calculated by averaging or summing together 8 current samples (of time T4, which in this case is a total of 64 A/D conversions) all acquired within current reading time interval T3. After calculating the current reading, a final current value may be calculated by averaging or summing together 5 current readings (which in this case is a total of 320 A/D conversions) all acquired within final current value time interval for first working electrode T2a or final current value time interval for second working electrode T2b. In an exemplary embodiment, methods will be described for using current readings and final current values for determining whether a test strip has been dosed with a physiological fluid, calculating a glucose concentration, performing error trapping procedures, and preventing a glucose test from initiating when ESD is injected into the test meter. Further, in accordance with other exemplary embodiments, different numbers of A/D conversions, samples, and reading may be used. Also, it may be possible to use a single working electrode or more than two working electrodes without departing from the scope of the invention.

In an exemplary embodiment, a final current value for first working electrode and a final current value for second working electrode may be summed together to give a grand summation. A glucose algorithm may include the steps of subtracting a background value (which is representative of general background noise and therefore represents a bias) from the grand summation followed by a division of a calibration slope (which calibrates the device to known glucose concentration/current curves or data) to generate a glucose concentration which can be outputted onto display 202. By using a method of the present invention of filtering the four highest and four lowest A/D conversion in the calculation of a current sample, a glucose concentration can be calculated that is sufficiently accurate and precise. Although this is one method of determining the glucose concentration, other methods may be applied to provide the final calculation, including look-up tables and other mathematical formulations. Similarly other processes may be used for different types of analytes.

The test current measured for a test strip 100 may have a characteristic shape as shown in FIG. 2 that is usually present when testing with a physiological fluid. If the characteristic shape is not present, then this is usually indicative of a system defect or a user error. More particularly, FIG. 2 shows an example of a test current that forms a maximum peak value followed by a gradual decay. In an exemplary embodiment, an error trapping method may include verifying that the test current does not increase after the maximum peak time Tp. The error trapping method may include determining a maximum peak value time and measuring a current reading at one second intervals as shown in FIG. 5 after applying fluid to test strip 100. The error trapping method may determine that there is no defect if a current reading minus an immediately previous current reading is less than an error threshold such as for example, about 100 nanoampres. This error trapping method may be performed on all current readings measured at one second intervals so long as the immediately previous current reading was measured after the maximum peak value time. As an example, if $ICR_k - ICR_{k-1} < 100$ nanoampres, then there is no error due to a non-characteristic increase in current with time where $ICR_k$ is the current reading at k seconds and $ICR_{k-1}$ is the current reading at k−1 seconds. However, if $ICR_k - ICR_{k-1} > 100$ nanoampres, then test meter 200 should output an error message on display 202 and not output a glucose concentration. Likewise, other data integrity or error trapping methods may be applied without departing from the scope of the invention.

In another exemplary embodiment, a simplified error trapping method may be used. In this simplified embodiment, only two current readings are used at four seconds and at five seconds. The current reading at four seconds may be subtracted from the current reading at five seconds. If ICR5−ICR4<100 nanoampres, then there is no error due to the non-characteristic increase in current with time, where ICR5 is the current reading at 5 seconds and ICR4 is the current reading at 4 seconds. However, if ICR5−ICR4>100 nanoampres, then test meter 200 should output an error message on display 202 and not output a glucose concentration. In this simplified exemplary embodiment, current readings are not used at one, two, and three seconds so as to simplify the error trapping algorithm. Additionally, maximum peak time Tp is also not calculated in this embodiment.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is

1. A testing meter for electrochemically measuring the concentration of an analyte in a physiological fluid sample, the testing meter comprising:
   a processor;
   an electrochemical measurement device that can be electrically connected to a test device comprising a fluid application portion having at least a pair of electrodes and a reagent so that the electrochemical measurement device can provide a potential and measure current flow across the at least a pair of electrodes when a test device is electrically connected to the electrochemical measurement device; and
   memory comprising programming that causes the electrochemical meter, when a test device is electrically connected thereto, to apply a constant voltage over a first predetermined time period and measure a current at the least a pair of electrodes and use the magnitude of the current at the end of the first predetermined time period as a test reading indicative of the concentration of an analyte in a physiological fluid present in the test fluid application area of the test device if the magnitude of the current remains above a threshold current value for a second predetermined time period wherein the second time period comprises an initial portion of the first time period.

2. The testing system of claim 1, wherein the duration of the second time period is greater than the time needed for a current spike from a predetermined extraneous event to decay below the threshold value and less than the first time period.

3. The testing system of claim 1, wherein the duration of the second time period is less than about 100 milliseconds.

* * * * *

UNITED STATES PATENT AND TRADEMARK OFFICE
CERTIFICATE OF CORRECTION

| | | |
|---|---|---|
| PATENT NO. | : 8,486,245 B2 | Page 1 of 1 |
| APPLICATION NO. | : 13/076413 | |
| DATED | : July 16, 2013 | |
| INVENTOR(S) | : Neil Roberts and Gary Smeaton | |

It is certified that error appears in the above-identified patent and that said Letters Patent is hereby corrected as shown below:

In the Claims:

Claim 1, column 14, line 14, delete "meter" and insert --measurement device-- and delete "a" and insert --the--.

Signed and Sealed this
Nineteenth Day of August, 2014

Michelle K. Lee
*Deputy Director of the United States Patent and Trademark Office*